US006693548B2

(12) United States Patent
Boyce et al.

(10) Patent No.: US 6,693,548 B2
(45) Date of Patent: Feb. 17, 2004

(54) STRUCTURAL MONITORING SYSTEM FOR HELICOPTER ROTOR COMPONENTS

(75) Inventors: William C. Boyce, Shelton, CT (US); Michael W. Hawman, Vernon, CT (US)

(73) Assignee: Sikorsky Aircraft Corporation, Stratford, CT (US)

( * ) Notice: Subject to any disclaimer, the term of this patent is extended or adjusted under 35 U.S.C. 154(b) by 0 days.

(21) Appl. No.: 09/924,909

(22) Filed: Aug. 8, 2001

(65) Prior Publication Data

US 2003/0030564 A1 Feb. 13, 2003

(51) Int. Cl.[7] .............................................. G08B 21/00
(52) U.S. Cl. ................. 340/657; 340/665; 340/870.16; 340/653; 340/661; 340/672; 73/660; 73/593; 73/649; 73/658; 73/687
(58) Field of Search ................................ 340/657, 665, 340/870.16, 653, 661, 672; 73/660, 593, 649, 658, 587

(56) References Cited

U.S. PATENT DOCUMENTS

| | | | |
|---|---|---|---|
| 3,924,456 A | | 12/1975 | Vahaviolos |
| 3,926,039 A | | 12/1975 | Zhukov et al. |
| 4,181,024 A | * | 1/1980 | Leak et al. .................... 73/660 |
| 4,524,620 A | | 6/1985 | Wright |
| 4,701,658 A | | 10/1987 | Ringermacher et al. |
| 5,065,630 A | | 11/1991 | Hadcock |
| 5,092,645 A | | 3/1992 | Okada |
| 5,109,700 A | * | 5/1992 | Hicho .......................... 73/660 |
| 5,195,046 A | | 3/1993 | Gerardi et al. |
| 5,383,133 A | * | 1/1995 | Staple ......................... 364/508 |
| 5,817,944 A | | 10/1998 | Chung |
| 5,852,793 A | * | 12/1998 | Board et al. .................. 703/56 |
| 6,076,405 A | * | 6/2000 | Schoess ........................ 73/587 |
| 6,176,136 B1 | * | 1/2001 | Zoppitelli et al. ............ 73/660 |
| 6,196,062 B1 | | 3/2001 | Wright et al. |
| 6,370,964 B1 | | 4/2002 | Chang et al. |

FOREIGN PATENT DOCUMENTS

| | | |
|---|---|---|
| DE | 29 37 709 A | 4/1981 |
| EP | 0 526 855 | 2/1993 |
| EP | 0 997 714 A | 5/2000 |
| JP | 05264517 | 10/1993 |

OTHER PUBLICATIONS

XP010226512, Apr. 21, 1997, Venkatesan G T.
XP001146521, 1985, W. C. Boyce.
Paper No. 2443–29, SPIE 1995 North American Conference on Smart Structures and Materials, San Diego, CA, Feb. 26–Mar. 3, 1995, entitled "Local–area health monitoring of aircra ft via piezoelectric actuator/sensor patches," by Z. Chaudhry, T. Joseph, F. Sun, C. Rogers.
SPIE vol. 3044, article entitled "Active Damage Interrogation System for Structural Health Monitoring" by Peter F. Lichtenwalner, James P. Dunne, Ronald S. Becker and Erwin W. Baumann.
Maintenance, Repair & Overall, article entitled "Inspection Methods 'Key' to Aging Aircraft Safety," by Edward H. Phillips/Dallas.

* cited by examiner

*Primary Examiner*—Daniel J. Wu
*Assistant Examiner*—Tai T. Nguyen
(74) *Attorney, Agent, or Firm*—Carlson, Gaskey & Olds

(57) ABSTRACT

A system for monitoring the structural condition of a helicopter rotor assembly component includes a piezoelectric sensor. Acoustic emission signal techniques allow for recognizing the relatively high frequency stress waves associated with the propagation of cracks or defects in a rotor assembly component. A signal conditioner processes the sensor signal and provides an output signal that includes at least one characteristic that is indicative of the content of the sensor signal and, therefore, the structural condition of the item of interest. A signal analyzer utilizes the output signal from the signal processor to determine the structural condition of the component.

14 Claims, 1 Drawing Sheet

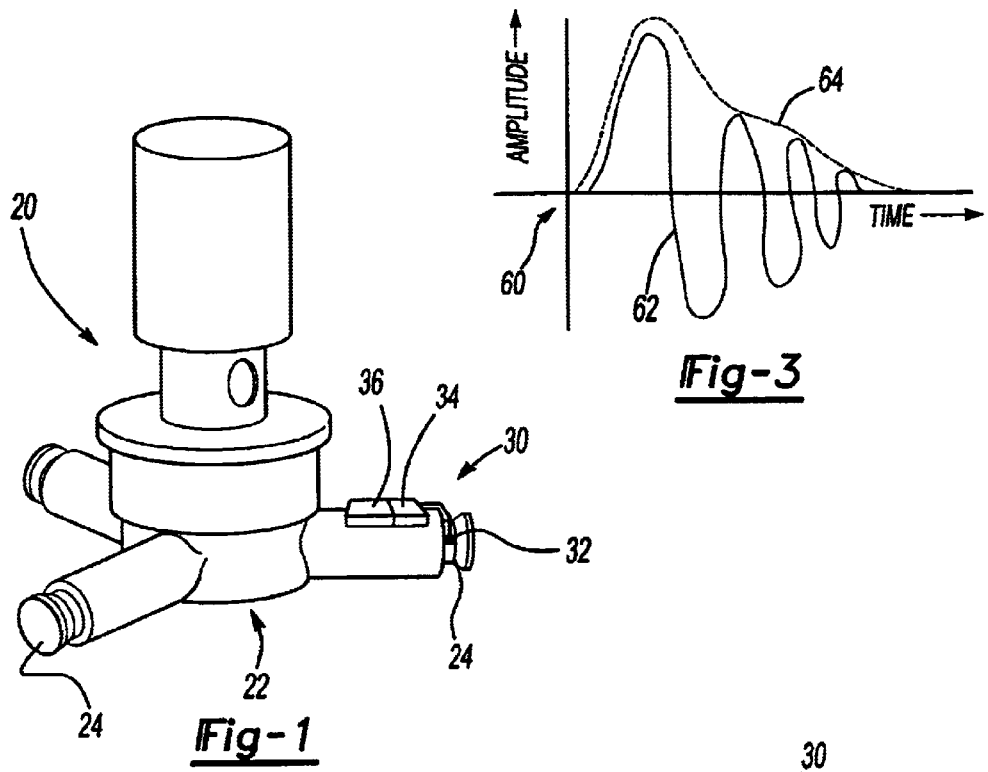
Fig-1
Fig-3
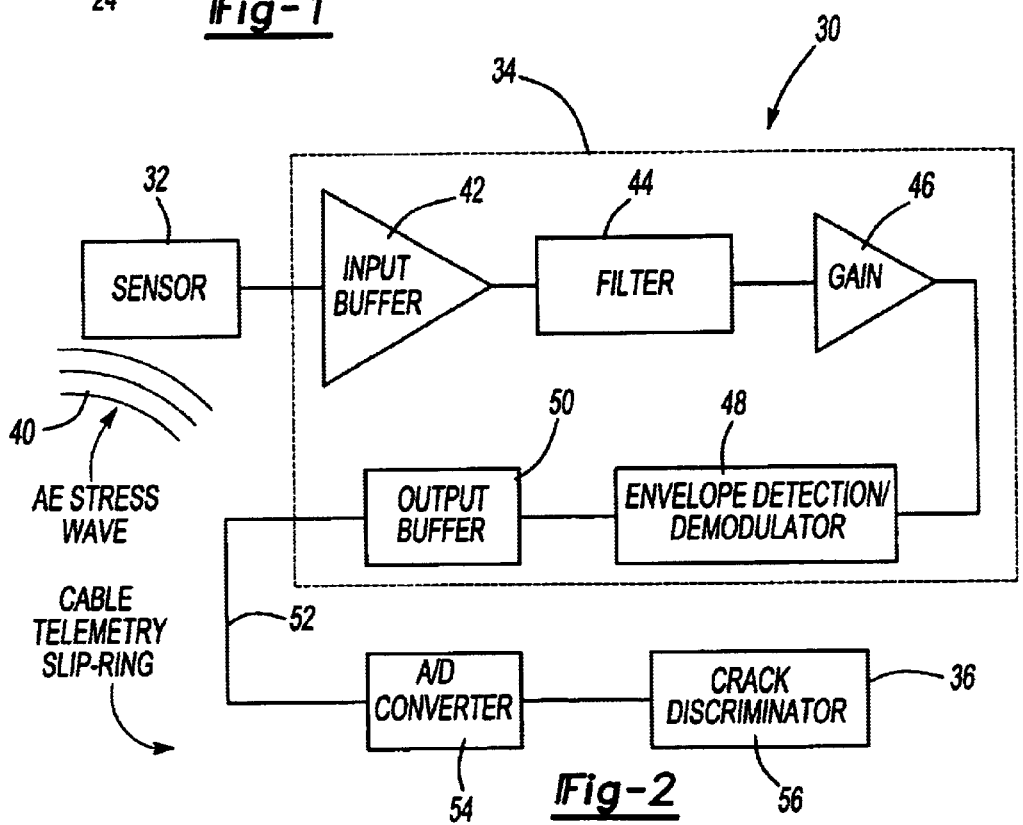
Fig-2

STRUCTURAL MONITORING SYSTEM FOR HELICOPTER ROTOR COMPONENTS

BACKGROUND OF THE INVENTION

This invention generally relates to structural condition monitoring. More particularly, this invention relates to monitoring the condition of components within a helicopter rotor assembly.

It has become increasingly desirable to monitor the structural condition of helicopter rotor components. Early detection of potential failures or fractures within the structural components provides the ability to perform preventative maintenance and avoid potential component failure.

One challenge associated with monitoring such components is the large amount of vibration that is normally associated with the components during helicopter operation. Such vibratory influences have traditionally presented noise that interfered with the ability to adequately detect any structural flaws.

More recent advances include the development of piezoelectric sensors that are capable of detecting stress energy within a component. An example of such sensors is shown in U.S. Pat. No. 4,071,658.

While such sensors have become available, their usefulness within certain applications has not been exploited. There is a need for appropriately treating a signal from such a sensor in order to derive useful information for a given situation.

This invention provides an acoustic emission-based system for monitoring the structural condition of a component within a helicopter rotor assembly.

SUMMARY OF THE INVENTION

In general terms, this invention is a system for determining a structural condition of a portion of a helicopter rotor assembly. The inventive system includes a piezoelectric sensor that can be supported on a portion of the rotor assembly. The sensor provides a signal indicative of stress waves in at least one portion of the rotor assembly. A signal processor processes the sensor signal and provides an output signal having at least one characteristic that is indicative of the content of the sensor signal. A signal analyzer receives the output signal and determines the structural condition based upon the output signal characteristic.

In the preferred embodiment, the signal processor includes a demodulator portion that demodulates the sensor signal to thereby generate an envelope representation of the sensor signal. The envelope representation is more readily transmitted to the signal analyzer and handled in a more efficient manner. The demodulated envelope signal, therefore, provides the necessary structural information without the complexity of the original sensor signal.

The various features and advantages of this invention will become apparent to those skilled in the art from the following detailed description of the currently preferred embodiment. The drawings that accompany the detailed description can be briefly described as follows.

BRIEF DESCRIPTION OF THE DRAWINGS

FIG. 1 schematically illustrates selected portions of a helicopter rotor assembly including a system designed according to this invention.

FIG. 2 schematically illustrates a system designed according to this invention.

FIG. 3 graphically represents signals used in this system.

DETAILED DESCRIPTION OF THE PREFERRED EMBODIMENT

FIG. 1 schematically illustrates a helicopter rotor assembly 20 that includes a hub portion 22. Only selected components of the rotor assembly 20 are illustrated for simplification purposes. One example component is a spindle 24, which is known in the art.

A system 30 for detecting the structural condition of the spindle 24 includes a sensor 32. Preferably, the sensor 32 detects acoustic emissions on the spindle 24, which are indicative of the structural condition of the spindle.

It must be noted that while the spindle 24 is discussed for illustration purposes, this invention is not limited to any particular component on a helicopter assembly. The sensor 32 preferably is a piezoelectric sensor. An example contact sensor is shown in U.S. Pat. No. 4,701,658. Other piezoelectric sensors are useful for this invention.

The sensor 32 communicates with a signal processor 34, which in turn communicates with a signal analyzer 36. While a separate signal processor 34 and signal analyzer 36 are schematically shown for discussion purposes, those skilled in the art will realize that a single computer or microprocessor, for example, could perform the functions described in association with the processor and analyzer of this description.

As schematically shown in FIG. 2, the signal processor 34 preferably provides an output signal that includes at least one characteristic that indicates the content of a signal from the sensor 32. When stress waves 40 are present within the component on which the sensor 32 is supported, those stress waves are detected by the sensor 32 that then provides an acoustic emission signal. The signal from the sensor 32 preferably is then input through a buffer 42 into the signal processor 34. A filter 44 preferably is tuned to filter out any low frequency components that are not part of the stress wave monitoring provided by the sensor 32. In one example, the filter filters out all signal components having a frequency below 100 KFz.

An amplifier 46 preferably amplifies the filtered signal before it is processed with a processor portion 48. In one example, the processor portion 48 is a demodulator that provides a signal that represents an envelope about the actual sensor signal. This envelope signal preferably then is processed through an output buffer 50 before being communicated over a communication link 52.

The communication link 52 may be a hard wire connection between the signal processor 34 and the signal analyzer 36. Alternatively, telemetry or other wireless communication strategies may be utilized. Radio frequency signals are one example. Another example communication link 52 is a slip ring, as known in the art. The choice of the particular arrangement will depend on the needs of a particular situation. Those skilled in the art who have the benefit of this description will be able to choose the components and arrangement that best suits their needs.

The processed signal preferably is converted into a digital signal using an analog to digital converter 54. The signal analyzer 36 preferably then utilizes information from the processed signal to determine the structural condition of the item of interest. The signal analyzer 36 preferably is a programmable microprocessor or portion of a microprocessor that is programmed using known phenomena and techniques for determining the structural condition of the item based upon the signal content.

The signal processor provides a more manageable form of signal that can be communicated to the signal analyzer 36. Having a manageable signal provides a significant advancement in allowing the acoustic emission technology available through piezoelectric sensors to be applicable for determining the structural condition of a helicopter rotor assembly component. The characteristics of the processed signal (in one example a demodulated envelope) provide enough information to make a structural condition determination. Preferably, the time/amplitude characteristic of the processed signal represents the overall shape of the original high frequency acoustic emission pulse. The enveloped signal, therefore, contains information regarding the high frequency content of the acoustic emission signal.

In the preferred embodiment, the primary feature of the processed signal that is used to make a structural condition determination is the rise time of the acoustic emission pulse. This invention recognizes the distinction between mechanical noise sources that have relatively longer rise times compared to the brief rise times associated with acoustic emissions indicating crack or other defect growth. Given this description, those skilled in the art will be able to develop empirical comparisons to determine the values of the rise time which are indicative of the structural condition of interest.

An example sensor signal is shown at 62 in the plot 60 of FIG. 3. The processed, envelope signal is shown at 64. As can be appreciated from FIG. 3, the rise time at the leading edge of the signal 64 is indicative of the rise time of the sensor signal 62. Therefore, the processed signal 64, which is more readily transmitted between components, provides an indication of the structural condition of the component of interest.

Additionally, other features of the process signal are used for determining the structural condition of the rotor component. Example signal characteristics include the amplitude, decay time, spectral content, pulse width, total energy, and frequency of occurrence. Known pattern classification techniques preferably are used to combine information regarding such signal features or characteristics to develop a strategy for determining structural condition.

Those who have the benefit of this description will be able to choose from among commercially available microprocessors or circuitry to accomplish the results provided by this invention. Likewise, those who have the benefit of this description will be able to develop the necessary software code to program the associated components.

The preceding description is exemplary rather than limiting in nature. For example, a spindle portion of a helicopter rotor assembly is used as an example component of which the structural condition is of interest. Other components, of course, can be monitored using a system designed according to this invention. Variations and modifications to the disclosed example may become apparent to those skilled in the art that do not depart from the purview and spirit of this invention. The scope of legal protection given to this invention should only be limited by the following claims.

We claim:

1. A system for determining a structural condition of a portion of a helicopter rotor assembly, comprising:

a piezoelectric sensor that is adapted to be supported on a portion of the rotor assembly and that provides a sensor signal indicative of stress waves in the portion of the rotor assembly;

a signal processor that processes the sensor signal and provides an output signal having at least one characteristic that is indicative of the content of the sensor signal, the signal processor including a demodulator portion that demodulates the sensor signal to thereby generate an envelope representation of the sensor signal; and a signal analyzer that receives the envelope representation output signal and determines the structural condition based upon the output signal characteristic.

2. The system of claim 1, wherein the signal analyzer utilizes an amplitude characteristic of the output signal.

3. The system of claim 1, wherein signal analyzer utilizes a time characteristic of the output signal.

4. The system of claim 1, wherein the output signal characteristic is indicative of a rise time of the sensor signal and wherein the signal analyzer utilizes the rise time information as an indicator of the structural condition.

5. The system of claim 1, wherein the signal processor includes a filter element that filters out sensor signal components outside of a chosen frequency range.

6. The system of claim 5, wherein the filter element filters out signal components that are below 100 KHz.

7. The system of claim 1, including a wire connection between the signal processor and the signal analyzer.

8. The system of claim 1, including a transmitter that transmits the output signal and a remotely located receiver associated with the signal analyzer that receives the transmitted output signal.

9. The system of claim 1, including a slip ring interface that communicates the output signal from the signal processor to the signal analyzer.

10. A method of determining a structural condition of a portion of a helicopter rotor assembly, comprising the steps of:

(A) attaching a piezoelectric sensor to a portion of the rotor assembly;

(B) detecting stress waves in the portion using the sensor;

(C) generating a stress signal indicative of the detected stress waves;

(D) demodulating the stress signal to generate an output signal that is an envelope representation of the stress signal and has at least one characteristic indicative of the content of the stress signal;

(E) determining the structural condition of the portion based upon the output signal characteristic.

11. The method of claim 10, including using at least one of the group of characteristics consisting of amplitude, time, energy, spectral content, pulse width and frequency as the characteristic of the output signal while performing step (E).

12. The method of claim 10, including using a rise time characteristic of the output signal while performing step (E).

13. The method of claim 10, wherein the output signal characteristic is indicative of a rise time of the stress signal and including using the rise time characteristic while performing step (E).

14. The method of claim 10, wherein step (D) includes removing selected frequency components prior to performing step (E).

* * * * *

UNITED STATES PATENT AND TRADEMARK OFFICE
CERTIFICATE OF CORRECTION

PATENT NO. : 6,693,548 B2
DATED : February 17, 2004
INVENTOR(S) : Boyce et al.

Page 1 of 1

It is certified that error appears in the above-identified patent and that said Letters Patent is hereby corrected as shown below:

Title page,
Item [*] Notice, please change to read as follows:
-- [*] Notice: Subject to any disclaimer, the term of this patent is extended or adjusted under 35 U.S.C. 154(b) by 16 days. --

Signed and Sealed this

First Day of June, 2004

JON W. DUDAS
*Acting Director of the United States Patent and Trademark Office*